United States Patent [19]

Taylor et al.

[11] Patent Number: 4,571,335
[45] Date of Patent: Feb. 18, 1986

[54] METHOD OF INHIBITING HERPETIC LESIONS BY THE USE OF PLATINUM COORDINATION COMPOUNDS

[76] Inventors: Robert C. Taylor, 3610 W. Drahner, Oxford, Mich. 48051; Sarah G. Ward, 53460 Mound Rd., Utica, Mich. 48087; Parbury P. Schmidt, 714 Cambridge Rochester, Mich. 84063

[21] Appl. No.: 505,216

[22] Filed: Jun. 17, 1983

[51] Int. Cl.⁴ .................... A61K 33/24; A61K 31/28; A61K 31/555
[52] U.S. Cl. .................... 424/131; 514/492; 514/184; 514/186
[58] Field of Search .................... 424/131

[56] References Cited

U.S. PATENT DOCUMENTS 4,053,587  10/1977  Davidson et al. .................... 424/131
4,255,417   3/1981  Bohm et al. .................... 424/131

Primary Examiner—Jerome D. Goldberg
Attorney, Agent, or Firm—Krass and Young

[57] ABSTRACT

A method is provided for inhibiting herpetic lesions associated with herpes virus infection in warm blooded animals comprising topically administering to any such warm blooded animal a lesion-inhibiting amount of antiherpes platinum coordination compound contained in a pharmaceutical composition in topical dosage form.

1 Claim, No Drawings

METHOD OF INHIBITING HERPETIC LESIONS BY THE USE OF PLATINUM COORDINATION COMPOUNDS

DESCRIPTION

TECHNICAL FIELD

This invention is directed to pharmaceutical means in composition or dosage form containing an antiviral component comprising a herpes virus inhibiting amount of platinum coordination compound and to a method of inhibiting lesions associated with herpes infection in warm blooded animals using the composition or dosage form.

BACKGROUND OF THE INVENTION

A wide variety of methods have been used over the years for the symptomatic relief of pain and remission of lesions such as fever blisters or cold sores associated with herpes infection attributed to herpes virus, particularly herpes simplex virus, type 1 or type 2. One way of treating the lesions presented by herpes virus infection calls for topical application on the lesion of a pharmaceutical formulation that contains idoxuridine as the active ingredient. Idoxuridine is an antimetabolite that interferes with DNA synthesis. It is poorly water-soluble and is used as a dilute solution in a suitable non-aqueous vehicle or solvent such as dimethylsulfoxide. Another way of treating herpes virus infection calls for topical application, on the lesion, of a formulation containing the antimetabolite vidarabine. However, attempts to eradicate genital or oral herpes virus infection by local application of vidarabine have failed to show substantial benefit.

It is known from U.S. Pat. No. 4,305,390 that cis-platinum diamino dichloride may be used as an activator in the presence of light, oxygen and an electric field to inactivate herpes simplex virus, type 1. It is also known from U.S. Pat. No. 4,053,587 to treat viral infection by parenteral administration of a composition in dosage form containing a platinum coordination compound as an active antiviral component. It has also been proposed in U.S. Pat. No. 4,255,417, concerning skin blemishes such as warts and moles, to apply topically a platinum compound to achieve disappearance of the treated blemish. However, treatment of herpetic lesions by the topical route using a platinum coordination compound in dosage form is not known.

In view of the limitations of current therapy for treatment of lesions associated with herpes virus infection, a need for additional therapeutic methods exists.

SUMMARY AND DETAILED DESCRIPTION

The present invention is based on the unexpected finding that platinum coordination compounds when topically applied in a suitable dosage form possess useful pharmacological properties for controlling and inhibiting herpetic skin lesions.

The invention in one aspect relates to a method of inhibiting herpetic lesions in warm blooded animals comprising:

applying to the surface of the lesions of any such warm blooded animal a herpes virus inhibiting amount of platinum coordination compound contained in a pharmaceutical composition in topical dosage form. The platinum coordination compound content, for purposes of the invention, can be that of a single compound or two or more compounds selected from the group of compounds comprising sub-groups (a) and (b), as follows:

(a) cisplatin,
cis-dichlorodihydroxy bis-isopropylamine platinum (IV),
diammine-1,2-cyclobutanedicarboxylatoplatinum (II),
1,2-diaminocyclohexane malonatoplatinum (II),
1,2-diaminocyclohexane sulphatoplatinum (II),
1,2-diaminocyclohexane hydroxmalonatoplatinum (II),
ethylenediamine malonatoplatinum (II), and
diammine ethylmalonatoplatinum (II), and (b) cisplatin derivatives having the formula $$cis\text{-}[Pt(NH_3)_2P_xCl_y]Cl_z$$

where x is one or two, y and z being one when x is one and being zero and two when x is two, and P is an antiviral compound of the group consisting of ara-A, acyclovir, ara-ADA, FIAC, FMAU, cyclaradine, and DHPG, also known as 9-β-D-arabinofuranosyladenine (ara-A or Vira-A), 9-[(2-hydroxyethoxy)methyl]guanine (acyclovir or Zovirax), the 2',3'-diacetate of ara-A (ara-ADA), 2'-fluoro-5-iodoarabinosylcytosine (FIAC), 2'-fluoro-5-methyl-arabinosyluracil (FMAU), the carbocyclic analog of ara-A (cyclaradine), and 9-(1,3-dihydroxy)-2-propoxymethyl)guanine (DHPG).

The invention in a preferred aspect relates to the method, as described, wherein the content of platinum coordination compound in the composition is solely that of cisplatin.

The invention in another preferred aspect relates to the method, as described, wherein the content of platinum coordination compound in the composition is that of a compound or compounds of sub-group (a). The structures and aqueous solubility of the latter compounds are tabulated as follows:

| Structural Formula | Compound | Aqueous Solubility (mg/ml) |
|---|---|---|
| 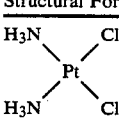 | cisplatin | 2.53 |
| 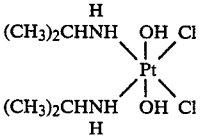 | cis-dichlorodihydroxy bis isopropylamine platinum (IV) | 20 |

-continued

| Structural Formula | Compound | Aqueous Solubility (mg/ml) |
|---|---|---|
| [structure] | diammine-1,1-cyclobutane dicarboxylatoplatinum (II) | 17.8 |
| [structure] | 1,2-diaminocyclohexane malonato platinum (II) | 0.2 |
| [structure] | 1,2-diaminocyclohexane sulphatoplatinum (II) | 12 |
| [structure] | 1,2-diaminocyclohexane hydroxymalonatoplatinum (II) | 0.20 |
| [structure] | ethylenediamine malonato platinum (II) | 6 |
| [structure] | diammine ethylmalonato platinum (II) | 57 |

The invention in another preferred aspect relates to the method, as described, wherein the content of platinum coordination compound in the composition is that of a compound or compounds of sub-group (b).

Pharmaceutical compositions contemplated by the invention can take any of a wide variety of topical dosage forms that may be prepared by conventional means. The compositions can be either solid or liquid. Solid form preparations include powders and suppositories. Suitable solid carriers are gelatin, low melting wax, cocoa butter, and the like.

Liquid form preparations include aqueous or nonaqueous solutions, suspensions, and emulsions. As an example may be mentioned water-propylene glycol solutions. Liquid preparations can also be formulated in solution in aqueous polyethylene glycol solution. Aqueous solutions can be prepared by dissolving the active component in water and adding suitable colorants, flavors, stabilizing, and thickening agents as desired. Aqueous solutions or suspensions suitable for topical use can be made by dissolving or dispersing the active component in water. The preparation may be non-aqueous, containing a penetration enhancer such as Azone (1-dodecyl-aza-cycloheptane-2-one) or dimethyl sulfoxide (DMSO) that serves to transport chemical through cellular membranes. The preparation may contain viscous material, e.g., natural or synthetic gums, resins, methyl cellulose, sodium carboxymethyl cellulose, and other thickening or suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, a solution, ointment, or powder in a vial, ampoule, or other container.

The quantity of active compound in a unit dose of preparation may be varied or adjusted according to the particular application.

In therapeutic use as a lesion-inhibiting agent, the compositions in one preferred embodiment are constituted in aqueous form, preferably as a concentrated or saturated aqueous solution of the antiviral platinum coordination compound. Cisplatin, for example is soluble in water or saline at about 2 mg./ml. Where the composition is a cream or ointment, the same is preferably aqueous, in which the water is concentrated or saturated with respect to the content of platinum coordination compound in the composition.

Cisplatin, suitable for purposes of the invention, is commercially available. For example, cisplatin is available under the name Platinol (R) Bristol, as a powder for constitution with water, sterile saline or other suitable vehicle. Other platinum coordination compounds described herein are known compounds or can be prepared as described herein.

In one preferred embodiment, the composition of the invention, is a solution of cisplatin in water, preferably a saturated solution of cisplatin. Unexpected features of the invention include the fact that the method utilizing a platinum coordination compound is highly effective with respect to remission and the further fact that, given the relative water-insolubility of platinum coordination compounds, only a relatively small quantity of the instant platinum solute is required. In another preferred embodiment the composition is an aqueous cream or ointment containing a minor proportion of cisplatin, preferably about 0.5 mg./ml. Administration is accomplished by applying the composition in suitable form such as a liquid, cream or ointment directly onto the surface of the lesion in an amount sufficient to cover the surface. Preferably application is made once or twice daily. For the treatment of facial cold sores, for example, two or three applications of the saturated aqueous solution, if early enough in the course of infection, are ordinarily sufficient to prevent the normal course of the infection. The normal course lasts from about 4 to 6 days and is characterized by increasing sensitivity followed by blisters or lesions, then a crust and scab with final sluffing of the scab. If applied early enough, no blister develops and hence no scab. An unexpected feature of the method is that in a substantial number of cases remission from oral skin lesions is maintained by the original treatment regimen for extended periods lasting in some cases up to a year or more. If the composition is not applied at the first symptom but later, then typically the normal course of the infection follows, with much less severity than if not treated, fewer blisters, smaller blisters and a smaller scab.

The preparation of cisplatin derivatives of formula cis-[Pt(NH$_3$)$_2$P$_x$Cl$_y$]Cl$_z$ contemplated by the invention is exemplified by the preparation of the cyclaradine derivative, as follows:

A 1-mmol amount of cisplatin is mixed with 2-mmol of cyclaradine in 100 ml of water heated to 50 degrees C. with constant stirring. The solution is heated in this manner for 5 hours. The heat source is then removed and the solution is stirred for an additional 24 hours and then filtered. The filtrate is rotary evaporated under low heat (40 degrees C.) to low volume (10 ml) and stored in a refrigerator overnight to precipitate any unwanted side products. The 10 ml portion is then rotary evaporated to dryness, treated with approximately 10 ml of acetone, and filtered. The off-white product is recrystallized by dissolving in a minimum amount of water and adding acetone. The product, cis-[Pt(NH$_3$)$_2$(cyclaradine)$_2$]Cl$_2$, is collected by filtration and dried in vacuo over Drierite; yield, 75% of theory.

By replacing cyclaradine in this procedure with a half-equivalent or an equivalent amount of each of the other antiviral compounds named in sub-group (b), one obtains the respective derivatives of that sub-group.

Having thus described our invention, the embodiments in which an exclusive property or privilege is claimed are defined as follows:

1. A method of eliminating herpetic lesions on the skin of a human comprising applying to the surface of each lesion a herpes virus lesion inhibiting amount of cisplatin contained in a pharmaceutical composition in topical dosage form.

* * * * *